United States Patent [19]

Niederer

[11] 4,359,785
[45] Nov. 23, 1982

[54] HIP JOINT PROSTHESIS

[75] Inventor: Peter G. Niederer, Zollikofen, Switzerland

[73] Assignee: Gebruder Sulzer, Aktiengesellschaft Protek A.G., Winterthur, Switzerland

[21] Appl. No.: 191,414

[22] Filed: Sep. 29, 1980

[30] Foreign Application Priority Data

Oct. 11, 1979 [CH] Switzerland .......................... 9216/79

[51] Int. Cl.³ ............................................... A61F 1/24
[52] U.S. Cl. .................................. 3/1.913; 128/92 CA
[58] Field of Search ........................ 3/1.913, 1.912, 1.9; 128/92 CA, 92 C

[56] References Cited

U.S. PATENT DOCUMENTS 3,829,904  8/1974  Ling et al. .............................. 3/1.912
4,021,865  5/1977  Charnley ................................ 3/1.913

FOREIGN PATENT DOCUMENTS 1409054  10/1975  United Kingdom ................. 3/1.913

Primary Examiner—Ronald L. Frinks
Attorney, Agent, or Firm—Kenyon & Kenyon

[57] ABSTRACT

In patients with hypoplastic hip joints, hip joint prostheses with relatively thin and narrow shank blades must be used. For this reason, due to the torque effect of the force acting on the joint head, the danger exists that deformations of the shank blades may occur. This danger is counteracted in that the collar type projection forming the transition between the shank and the prosthesis neck extends in a direction parallel to the prosthesis neck, preferably in a prolongation of the lower edge of the prosthesis neck.

3 Claims, 3 Drawing Figures

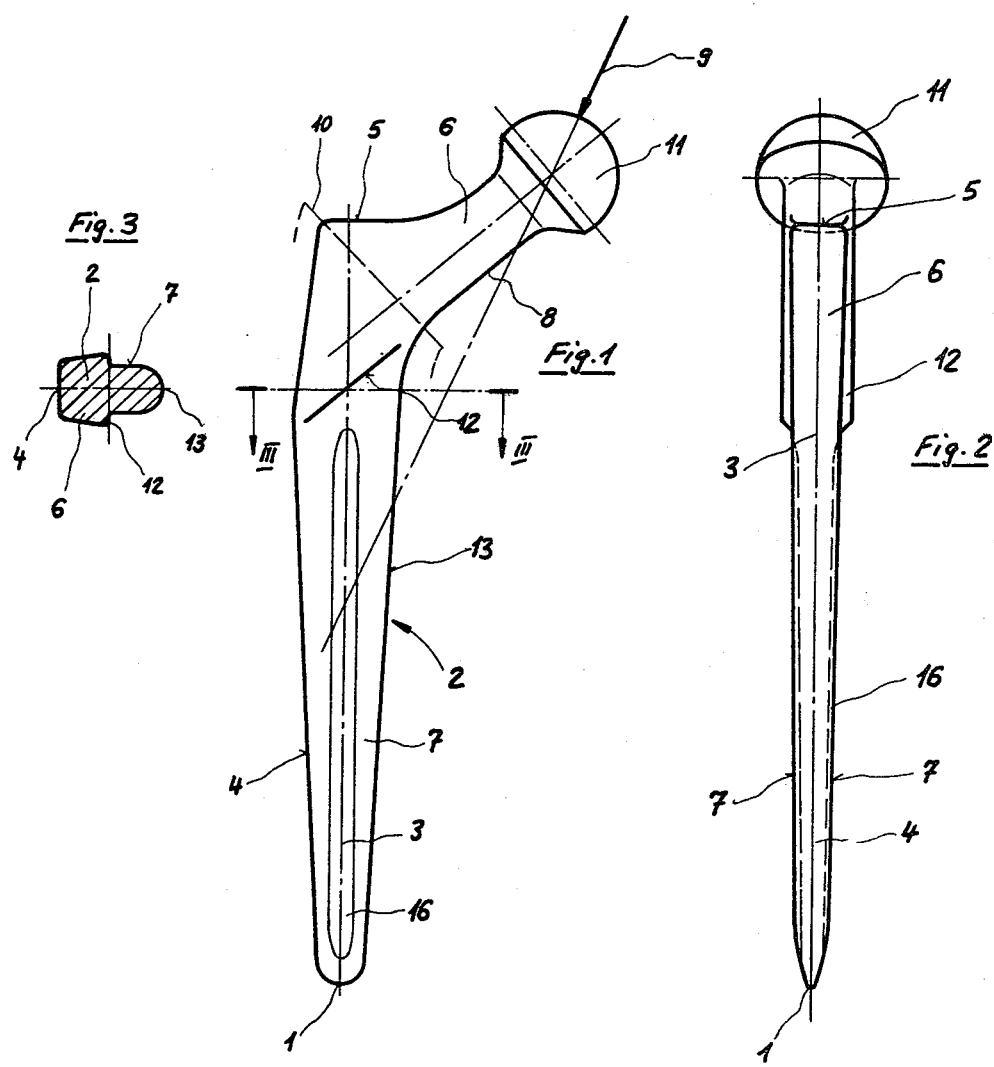

HIP JOINT PROSTHESIS

This invention relates to a hip joint prosthesis.

Heretofore, various types of prostheses have been known for implanting in femurs in order to form a hip joint. For example, hip joint prostheses have been formed with a straight blade type shank for anchoring as by a wedging action and through a cement bed in a femur. In some cases, the shank first widens conically from a free distal end symmetrically of a longitudinal median axis of the shank and then, at a point about three-quarters along the shank, bevels inwardly along the narrow lateral side towards the shank axis. The opposite narrow medial side, in these cases, passes along a smooth curve in stepless manner into a neck of the prosthesis. In addition, a collar-type projection is formed between the shank and the neck and a joint head is carried at the end of the neck.

Hip joint prostheses of a similar kind are known, for example from the journal "Orthopadie" 8, (1979), page 73, 74, and in particular FIG. 1. The so-called straight shank of this prosthesis is intended to be wedged in a hollow space of a medullary cavity, which has been surgically matched to the shank and filled with a bed of bone cement in such a way that the cement bed or cement quiver is largely relieved from carrying loads. The carrying support of this prosthesis takes place primarily by jamming along the narrow medial and lateral sides of the shank.

In the usual prosthesis constructions, the collar which separates the neck from the shank of the prosthesis extends substantially perpendicular to the axis of the prosthesis neck. The collar is thus essentially parallel to the sectional plane through the neck of the femur. As such, the collar is additionally supported on the edge of the cement quiver within the bone and prevents the shank from sinking into the bone cement.

Because the prosthesis neck acts as a "lever" the load acting on the joint head causes a torque effect by which the relatively thin blade of the prosthesis is placed under a relatively large bending and torsional stress. In patients with hypoplastic hip joints, the femur is generally malformed and crippled in the region of the neck and of the joint head. Also, the medullary space is often extremely narrow. Thus, prostheses of the above mentioned type for these diseases are therefore relatively thin and provided with a relatively narrow blade. However, because of the torque referred to, plastic deformations may result in the relatively thin and narrow blade of these prostheses.

Accordingly, it is an object of the invention to prevent plastic deformations in the shank of an implanted hip joint prosthesis.

It is another object of the invention to prevent twisting of a hip joint prosthesis in a femur due to loads applied on a head of the prosthesis.

It is another object of the invention to provide a hip joint prosthesis which can be firmly anchored in a femur.

Briefly, the invention provides a hip joint prosthesis which includes a shank for anchoring in a cement bed in a surgically prepared femur, a neck and a collar-like projection between the shank and neck.

The shank has a longitudinal median axis, a narrow blade-like portion extending from a distal end with a conical taper symmetrically of the longitudinal axis to define a narrow lateral side and a narrow medial side, a beveled side extending from the lateral side at an angle inwardly toward the longitudinal axis and an arcuate side extending from the medial side on a radius of a circle.

The neck is angularly disposed relative to the axis of the shank and has a lower edge connected to the arcuate side of the shank.

The projection extends at least approximately in the direction of the neck relative to the shank.

The prosthesis is constructed so that in the region of critical loads, the shank is reinforced. Thus, even in the case of thin narrow shanks for dysplasia patients, plastic deformation need not be feared. Further, the position of the neck allows the neck to be braced directly in the bone in the region of the medial calcarine arc. Thus, there is a further reduction in the torque exerted by a load on the prosthesis. Moreover—as is the case with a collar of a conventional prosthesis—good support of the prosthesis in the cement is made possible.

The desired effect of the prosthesis can be improved if the collar-like projection extends at least approximately in alignment with the lower edge of the neck of the prosthesis. Thus, the prosthesis neck is understood functionally to be a part of the prosthesis shank, because—in contrast to the usual prosthesis—the neck takes over a part of the bracing in the bone and cement.

These and other objects and advantages of the invention will become more apparent from the following detailed description taken in conjunction with the accompanying drawings wherein:

FIG. 1 illustrates a front view of a hip joint prosthesis according to the invention;

FIG. 2 illustrates a side view of the prosthesis of FIG. 1 taken from the left; and FIG. 3 illustrates a view taken on line III—III of FIG. 1.

Referring to FIGS. 1 and 2, the hip joint prosthesis has a shank 2 for anchoring in a cement bed (not shown) in a surgically prepared femur. As shown, the shank 2 has a longitudinal medial axis 3 with a narrow blade-like portion extending from a distal end with a conical taper symmetrically of the axis 3. This portion defines a narrow lateral side 4 and a narrow medial side 13. At a level about ¾ up the shank 2, the lateral side 4 has a discontinuity from which a beveled side extends at an angle inwardly towards the axis 3 to terminate in an, at least, nearly horizontal shoulder 5 (i.e. the shoulder 5 is perpendicular to the axis 3). At a level slightly above this discontinuity, the medial side 13 of the shank has an arcuate side extending on a radius from the conical taper upwards.

The prosthesis also has a neck 6 angularly disposed relative to the axis 3 of the shank 2. This neck 6 includes a lower edge 8 which is connected to the arcuate side of the shank portion (see FIG. 1). Thus, the medial side 13 of the shank 2 is connected in a smooth stepless manner to the lower edge 8 of the neck 6, while the shoulder 5 forms a transition from the shank 2 to the neck 6. In addition, the neck 6 carries a joint head 11 on the free end to receive a main load in the direction indicated by the arrow 9.

Referring to FIGS. 1 and 3, a collar-like projection 12 is disposed between the shank 2 and the neck 6 and extends at least approximately in the direction of the neck 6 relative to the shank 2. The projection 12 extends from the relatively thin and narrow shank portion and forms a transition to the thicker neck 6. The height of the projection 12 is chosen so that the projection 12 is a prolongation of the lower edge 8 of the neck 6.

With the prosthesis correctly inserted in a cement bed, the collar 12 and the prolonged neck 6 extending from the collar 12 to the shoulder 5 are practically completely submerged in the cement bed or at least largely so, as is indicated in FIG. 1 by the broken line 10, representing approximately the upper limit of the cement bed. Regardless of where the pivot point for the torque occurring due to the eccentric load must be assumed on the collar 12, a secure anchoring of the shank in the cement and bone bearing is thereby obtained. In addition, the chance of a plastic deformation of the shank 2 occurring is diminished.

As shown in FIGS. 1 and 2, longitudinal grooves 16 are formed in side walls 7 of the shank portion. In addition, these side walls 7 terminate at the distal end in a circular arc which extends from the lateral side 4 to the medial side 13 while coming to a point with a relatively large radius (FIG. 2). This latter curvature is chosen so that, to the extent possible, there is smooth transition of the loading forces from the shank 2 and then to the spongy bone tissue which may be compacted upon driving in of the prosthesis.

The invention thus provides a hip joint prosthesis which can be used for patients with hypoplastic hip joints without plastic deformation of a thin blade-like shank.

What is claimed is:

1. A hip joint prosthesis comprising
   a shank for anchoring in a cement bed in a surgically prepared femur, said shank having a longitudinal median axis, a narrow blade-like portion extending from a distal end with a conical taper symmetrically of said axis to define a narrow lateral side and a narrow medial side, and a beveled side extending from said lateral side at an angle inwardly toward said axis and an arcuate side extending from said medial side on a radius of a circle;
   a neck angularly disposed relative to said axis of said shank and having a lower edge connected to said arcuate side of said shank; and
   a collar-like projection between said shank and said neck, said projection extending at least approximately in the direction of said neck relative to said shank.

2. A hip joint prosthesis as set forth in claim 1 wherein said projection is aligned with said lower edge of said neck.

3. A hip joint prosthesis as set forth in claim 1 which further comprises a shoulder between said neck and said shank, said shoulder being disposed perpendicularly of said axis of said shank.

* * * * *

UNITED STATES PATENT AND TRADEMARK OFFICE
CERTIFICATE OF CORRECTION

PATENT NO. : 4,359,785
DATED : November 23, 1982
INVENTOR(S) : Peter Gino Niederer It is certified that error appears in the above—identified patent and that said Letters Patent is hereby corrected as shown below:

Col. 2, line 63, change "and" to -- to --.

Signed and Sealed this

Nineteenth Day of April 1983

[SEAL]

Attest:

GERALD J. MOSSINGHOFF

Attesting Officer

Commissioner of Patents and Trademarks